United States Patent [19]

Seyffart et al.

[11] Patent Number: 4,879,280
[45] Date of Patent: Nov. 7, 1989

[54] DIALYSIS SOLUTION FOR USE IN INTRAPERITONEAL DIALYSIS

[75] Inventors: Günther Seyffart; Wolfgang Rothe, both of Oberursel; Volker Bartz, Giessen, all of Fed. Rep. of Germany; Volker Bartz, Giessen, all of Fed. Rep. of Germany

[73] Assignee: Fresenius AG, Bad Homburg, Fed. Rep. of Germany

[21] Appl. No.: 783,802

[22] Filed: Oct. 4, 1985

Related U.S. Application Data

[63] Continuation of Ser. No. 420,574, Sep. 20, 1982, abandoned.

[30] Foreign Application Priority Data

Sep. 24, 1981 [DE] Fed. Rep. of Germany ....... 3138104

[51] Int. Cl.[4] .............................................. A61K 31/70
[52] U.S. Cl. .......................................... 514/53; 514/54
[58] Field of Search ...................... 514/53, 59, 60, 54

[56] References Cited

U.S. PATENT DOCUMENTS

| | | | |
|---|---|---|---|
| 3,911,915 | 10/1975 | Seifter et al. | 514/23 |
| 3,983,232 | 9/1976 | Pekic et al. | 536/112 |
| 4,182,756 | 1/1980 | Ramsay et al. | 514/23 |
| 4,238,482 | 12/1980 | Peyman et al. | 536/112 |
| 4,308,255 | 12/1981 | Raj et al. | 514/59 |
| 4,322,407 | 3/1982 | Ko | 514/23 |

FOREIGN PATENT DOCUMENTS

| | | |
|---|---|---|
| 76355 | 4/1983 | European Pat. Off. |
| 83/0087 | 1/1983 | PCT Int'l Appl. |

OTHER PUBLICATIONS

Chemical Abstracts, vol. 98 (1983) No. 142001y.

Primary Examiner—Johnnie R. Brown
Assistant Examiner—Elli Peselev
Attorney, Agent, or Firm—Cushman, Darby & Cushman

[57] ABSTRACT

An aqueous solution for use in intraperitoneal dialysis made up of least one substance for regulation of the electrolyte balance in the body of the patient has a saccharide with at least one glycosidic bond, such as more specially, disaccharides (for example saccharose, maltose and/or lactose) at a level of 0.08 to 0.24 m/l.

8 Claims, No Drawings

DIALYSIS SOLUTION FOR USE IN INTRAPERITONEAL DIALYSIS

This is a continuation of application Ser. No. 420,574, filed Sept. 20, 1982, which was abandoned upon the filing hereof.

BACKGROUND OF THE INVENTION

The present invention is with respect to a dialysis solution for use in intraperitoneal dialysis having an osmotically active substance in the form of a saccharide and with at least one further substance for regulation of the electrolyte balance, in the form of an aqueous solution.

Patients with serious renal disorders or with complete renal failure have in the past had to make use of an artificial kidney for treatment every two to three days. In the case of this treatment, in addition to water which was no longer able to be excreted by the patient, metabolic products were taken from the patient's body in a generally short stretch of time, that is to say at a rate which was frequently responsible for complications such as a general malaise, vomiting and the like. Furthermore the patient had to be kept in bed at the time of the treatment and was not able to go on working.

It was for these reasons that there has of late been the development of a new treatment for clearing metabolic products and excess water from the body of a patient with renal disease, which is named intraperitoneal or continuous ambulatory peritoneal dialysis (CAPD), in which a dialysis or irrigation solution is run through a sterile pipe into the patient's peritoneal cavity, so that, using the peritoneum as a dialysis membrane, more or less the same effect as a dialysis filter is produced. The solution is kept in the peritoneal cavity for a certain stretch of time, that is to say till not only the water but furthermore the products of metabolism have been cleared from the patient's body to the desired degree. At the end of the treatment, the bag, in which the solution was stored in the first place before the start of the treatment, is placed at a lower level than the outlet in the body wall of the patient for running the solution out of the patient's body back in to the said bag.

This treatment takes place continuously so that the waste products are able to be cleared from the body at a much slower rate over a given length of time, this being very important for the well-being of the patient and furthermore he or she is on his or her feet and may keep on with normal everyday work. A further useful effect is that this form of treatment puts an end to inflammation of the blood vessels likely to be caused by tubes piercing them, as has been necessary for treatment using artificial kidneys so far.

For clearing excess water from the body of a patient, it is necessary for the aqueous CAPD solution to be made up with a osmotically active substance, that is to say one responsible for causing the water to make its way through the peritoneum into the dialysis solution; furthermore the said solution has to have a certain level of electrolyte for keeping up, or for regulation of the electrolyte balance in the body.

Presently the osmotically active substance which is more widely used than any other for this purpose is glucose, although its effect does become less as dialysis takes place, because it is absorbed in quite large amounts by the body. In fact, glucose levels of as high as 300 mg/100 ml of blood are likely on dialysis, something which is very damaging in the case of diabetes, that frequently goes hand in hand with renal disease. Such a glucose uptake may in fact be responsible for hyperglycemic shocks and it may be seen that the administration of strong glucose solutions will be a metabolic risk factor, seeing that the insulin dosage rate is hard to get worked out for increased blood sugar levels. This question is not to be overlooked because 20% of all renal patients have diabetes. A wrong adjustment of the glucose level may be responsible for conditions even as serious as a diabetic coma.

Furthermore the excess resorption of glucose will be the cause of the patient taking up overly much water, that is to say there is osmosis in the wrong direction (reverse osmosis) and the dialytic effect is turned round and put to an end. Further disorders which are to kept an eye on are the building up of excess fat because of metabolic troubles, hypertriglyceridemia and arterosclerosis caused by the increased glucose uptake.

Because of this undesired resorption of glucose in dialysis, in the prior art experiments have been made with suger substitutes as for example fructose, sorbite, xylite and others, see Proc. Europ. Dial. Transpl. Ass. 6 (1969), page 300; Ann. Intern. Med. 79 (1973) page 511.

One using fructose however the outcome was again the resorption of as high levels as was the case with glucose and the same undesired effects were to be seen, although however fructose is better tolerated by diabetics and may be degraded in the liver quickly. A specially undesired effect is that fructose dialysis solution is the cause of irritation of the peritoneum and for this reason is responsible for an unpleasant feeling on the part of the patient.

The use of polyol-based sugar substitutes such as sorbite is likely to be troublesome inasfar as such substances are not as a rule able to be metabolized and are stored in the body because they are not able to be excreted. Mannite, as a further example, is stored in the brain after being resorbed, and this is likely to be the cause of serious brain damage.

On the other hand, by way of parenteral nutrition, suggestions have been made in German Pat. Nos. 2,035,674, 2,429,034 and 2,642,714 for the use of different sugar components. However parenteral nutrition of a patient by infusion right into the blood is quite different in nature to the use of a CAPD dialysis solution, in which the most important points are clearing excess water from the body and electrolyte exchange. For this reason it is not possible for such parenteral nutrition solutions to take the place of a dialysis solution for CAPD.

ACCOUNT OF THE INVENTION.

For these reasons one purpose of the invention is that of designing a solution for intraperitoneal dialysis of the sort noted, which is well tolerated by diabetics.

A further purpose of the invention is that of compounding such a solution not causing irritation of the peritoneum.

A still further purpose of the present invention is that of making up such a solution, that inasfar as it is resorbed by the body, is metabolized or degraded in the human body at a later stage.

For effecting these and further purposes, in the present invention a dialysis solution for intraperitoneal dialysis in the form of an aqueous solution of a saccharide as an osmotically active substance and at least one substance for regulation of the electrolyte balance, is characterized in that the saccharide is made up of at least two monosaccharide anhydrides.

Further useful forms of the invention will become clear from the more detailed account now to be given and from the claims.

The invention is based on the surprising new fact that dialysis solutions, which are made up with the special sugars of the present invention, such as disaccharides in the form of saccharose, maltose, and/or lactose have a first rate osmotic activity without any amounts, great enough to be important, of sugar being absorbed by the body. Unlike dialysis solutions compounded with glucose, it is only small amounts of the sugars in the solution of the present invention that are converted and resorbed in the cells of the peritoneum, this probably being because of the stepped-up osmotic activity of these sugars. This effect is probably oppositely directed to the resorption so that such solutions keep their full activity over long stretches of time and no backward or reverse osmosis in is caused in this case.

Furthermore the dialysis solution of the present invention is well tolerated by CAPD patients, that is to say, there is no irritation of the peritoneum.

Even if in fact cleavage of these sugars takes place into glucose units, the glucose level then produced in the blood is very much lower than that caused by a prior art glucose solution and because of this the control of the glucose level in the blood, so important for diabetics, may readily be then be undertaken by the administration of the right amount of glucose.

Saccharides that may be used in the present solutions with at least two monosaccharide anhydrides are for example the disaccharides, the trisaccharides, further oligosaccharides and polysaccharides, that, as is now to be made clear, are not to have a molecular weight greater than 400,000.

Examples of disaccharides are: lactose, saccharose, maltose, trehalose, cellobiose, gentiobiose, melibiose, and rutinose. Of these disaccharides the natural ones and those of which large amounts are on hand, are preferred, that is to say, saccharose, lactose and/or maltose.

An example of an oligosaccharide, made up of three monosaccharide anhydrides, is raffinose.

Polysaccharides which may be used in the present invention, are those which are at least colloidally soluble in water, that is to say for example starch and more specially products made by degrading it down to a molecular weight of under 3,000, such as inulin, pectin and the like. While these polysaccharides are natural, other, that is to say artificial polysaccharides as for example dextrans and the like may be used as well. These dextrans are used for example as a substitute for volume and have a molecular weight of for example 40,000. A further family of substances that may be used in the present invention is made up of the hydroxy-ethyl starches (HES), as well used as volume substitutes or extenders. A preferred substance made by degrading dextrans is marketed by Knoll of Ludwigshafen, Germany, under the tradename of Hapten with a MW. of about 1,000.

The natural osmotic pressure of blood is about 280 mosm/1 so that it is necessary to have a greater value than this in order to get osmosis into the dialysis solution through the peritoneum going. In this respect the solution has to have such a sugar level that it has an osmotic pressure of 300 to 700 and more specially 320 to 550, or, put in the form of a more limited range, of 350 to a value of 450.

As a rough rule, the levels of sugar present in the solution will be 0.02 to 0.3, and more specially 0.08 to 0.24 m/1, the last-named range answering to the osmotic pressure range noted as being more specially preferred.

It will be seen from this that these molar amounts are controlling for the said top limit of the molecular weight, seeing that polysaccharides with higher molecular weights give solutions which are no longer flowable, flowing properties however being a condition for use as a solution in CAPD.

Dialysis solutions of the invention are made up with saccharose, maltose and/or lactose as more specially preferred disaccharides, and they may be used singly or mixed together, in amounts of roughly 15 to roughly 150 and more specially 30 to 85 g/l.

Such disaccharides are on the market in a highly pure form, that is to say with a degree of purity of 99% upwards so that they are generally free of impurities likely to be harmful to the body.

Alongside these osmotically active substances, the dialysis solution of the present invention has to be made up with substances for regulation of the electrolyte balance of the CAPD patient, because otherwise there will be a breakdown thereof and the patient may be put into great danger in some cases.

Because the sodium balance of kidney patients is generally normal, the sodium level in the new dialysis solutions will be about the same as in the body fluids, that is to say roughly 130 to 147 mmole/1.

Because the potassium level is very much increased from the normal level of 4 to 4.8 mmole/1, it is best for the level of potassium ions in the new dialysis solution to be about 1.5 to 3 and more specially 2 mmole/1.

The overgreat supply of calcium from outside sources puts the patient's calcium level up somewhat as well so that the calcium level in the new dialysis solution is best put at a level of about 1.7 to 2.1 mmole/1.

The amount of magnesium is as well some increased so that the magnesium level in the new dialysis solution is best stepped up to about 0.4 to 0.6 mmole/1.

On the other hand, the chloride level in the new dialysis solution is best put at the physiological value of 100 to 110 mmole/1, seeing that the value is generally normal in a patient with renal disease.

Renal patients are more specially likely to have forms of acidosis so that there is an increase in the hydrogen ion level and this may be decreased again by administration in the right amounts of bases or substances responsible for forming bases, as for example the lactate ion that is burned in the patient's body in the citric acid cycle with the outcome that a dose of sodium lactate is in the end responsible for forming sodium hydroxide, the same trapping hydrogen atoms. In this respect it has been seen in connection with the present invention that a useful effect is produced by the administration to the patient of the new solution with lactate or acetate (which is used up in the body as well) at a rate of about 20 to 60 and more specially 35 mmole/1.

The new dialysis solution may be produced under normal, sterile conditions. To take an example, the saccharide to be used in the invention, together with the desired amount of electrolyte and generally free of pyrogens and of any further impurities are made up into a water solution, the water being of a quality as normally used for such purposes. Then the solution is run through a bacterial filter so as to be sterile or made sterile by heating under pressure.

The solution is then filled up into a bag, which is best placed within another bag, the space therebetween being filled with the new solution as well to make certain of the inner bag's being completely sterile.

For administration of the new dialysis solution a pipe system of the right design is used, it running through the wall of the patient's abdomen so that the solution makes it way into the peritoneal cavity, where it is then kept till the patient has given up the desired amount of water (by osmosis) and the desired amount of electrolyte (by diffusion).

EXAMPLES OF THE INVENTION.

Example 1.

Using one liter of injection-quality water a solution was made up of of 0.08, 0.13 and in the other case 0.23 mole/l of saccharose and as much electrolyte salts in the form of acetate and chloride that one liter of solution on assay gave:

Na+: 134 mmole/l
K+: 2 mmole/l
Ca2+: 1.75 mmole/l
Mg2+: 0.5 mmole/l
Cl-: 105.5 mmole/l
Lactate-: 35 mole/l This solution was then filtered and sterilized.

It had a theoretical osmotic pressure of 360 (with 0.08 mole saccharose), of 395 (with 0.13 mole saccharose) and of 510 (in the case of 0.23 mole saccharose) mosm/l.

Example 2

The solution was made up as in example 1 but using maltose in place of saccharose.

Example 3

The solution was made up as in example 1 but with lactose in place of sacchrose.

Example 4

In place of the saccharose as in example 1 equal mixed amounts of lactose and maltose were used.

Example 5

The solution of example 1 was made up using the said Hapten as an oligosaccharide in place of the sacchrose.

We claim:

1. A method of intraperitoneal dialysis comprising: introducing an aqueous composition into the patient's abdomen such that said composition makes its way into the peritoneal cavity of said patient, said composition comprising:
a saccharide as an osmotically active substance and at least one substance for regulating the electrolyte balance in the patient, said saccharide is selected from the group consisting of lactose, saccharose, trehalose, celloboise, gentioboise, meliboise, rutinose, inulin, pectin, and raffinose, the amount of said saccharide being sufficient such that the said composition has an osmotic pressure of 300 to 700 mosm/l.

2. The method according to claim 1 wherein said saccharide is present in said composition in an amount of about 15 to 150 grams per liter.

3. The method according to claim 1, wherein said saccharide is present in the solution in an amount of about 0.08–0.24 m/l.

4. The method according to claim 1, wherein said composition contains injection-quality water and about 0.08 to 0.24 mole/liter of said saccharide.

5. The method according to claim 4 wherein said composition contains about 130 to 147 mmole/liter of sodium ions, about 1.5 to 3 mmole/liter of potassium ions, about 1.7 to 2.1 mmole/liter of calcium ions, and 0.4 to 0.6 mmole/liter of magnesium ions.

6. The method according to claim 4 wherein said composition contains about 20 to 60 mmole per liter of lactic ions or acetate ions.

7. The method according to claim 1 wherein said composition comprises about 0.08 to 0.24 mole/liter of said saccharide and electrolyte salts in the form of acetates and fluorides, said composition giving upon assay:

Na+: 134 mmole/l
K+: 2 mmole/l
Ca$^{2+}$: 1.75 mmole/l
Mg$^{2+}$: 0.5 mmole/l
Cl−: 105.5 mmole/l
lactate−: 35 mmole/l.

8. The method of intraperitoneal dialysis comprising: introducing an aqueous composition into the patient's abdomen such that said composition makes its way into the peritoneal cavity of said patient, said composition comprising 134 mmole/l sodium ions, 2 mmole/l of potassium ions, 1.75 mmole/l of calcium ions, 105.5 mmole/l of chloride ions, and 35 mmole/l of lactate ions together with 0.08 to 0.23 mole/l of a saccharide selected from the group consisting of saccharose, maltose, lactose, and mixtures thereof such that said composition has an osmotic pressure of 300 to 700 mosm/l.

* * * * *